United States Patent

Nasu

[11] Patent Number: 5,925,088
[45] Date of Patent: Jul. 20, 1999

[54] AIR-FUEL RATIO DETECTING DEVICE AND METHOD

[75] Inventor: Masahiro Nasu, Susono, Japan

[73] Assignee: Toyota Jidosha Kabushiki Kaisha, Aichi, Japan

[21] Appl. No.: 08/591,787

[22] Filed: Jan. 25, 1996

[30]       Foreign Application Priority Data

Jan. 30, 1995   [JP]   Japan .................................. 7-012325

[51] Int. Cl.⁶ .............................. G06G 7/70; F02D 41/00; G01N 7/00
[52] U.S. Cl. .......................... 701/103; 701/101; 701/102; 123/686; 123/491; 123/693; 73/23.32; 73/117.3
[58] Field of Search ......................... 364/431.01, 431.03, 364/431.04, 431.051, 431.052, 431.053, 431.061, 431.062; 60/276, 277, 274, 285, 684, 6; 123/424, 428, 493, 686, 674, 685, 694, 681, 684, 693, 697, 689, 695, 688; 701/101, 102, 103, 104, 105; 73/233.2, 25.03, 117.3, 118.2; 204/406, 425, 401, 410, 412, 426, 421

[56]              References Cited

U.S. PATENT DOCUMENTS

| | | | |
|---|---|---|---|
| 4,130,095 | 12/1978 | Bowler et al. | 123/675 |
| 4,306,444 | 12/1981 | Hattori et al. | 73/23.32 |
| 4,344,317 | 8/1982 | Hattori et al. | 73/23.32 |
| 4,348,727 | 9/1982 | Kobayashi et al. | 701/104 |
| 4,363,306 | 12/1982 | Sone et al. | 123/440 |
| 4,440,621 | 4/1984 | Kitahara et al. | 123/489 |
| 4,458,319 | 7/1984 | Chujo et al. | 701/109 |
| 4,534,330 | 8/1985 | Osuga et al. | 73/23.32 |
| 4,548,179 | 10/1985 | Ninomiya et al. | 123/684 |
| 4,592,325 | 6/1986 | Nakagawa | 123/489 |
| 4,718,999 | 1/1988 | Suzuki et al. | 204/406 |
| 4,729,220 | 3/1988 | Terasaka et al. | 60/285 |
| 4,751,907 | 6/1988 | Yamamoto et al. | 123/489 |
| 4,753,203 | 6/1988 | Yamada | 73/23.32 |
| 4,823,270 | 4/1989 | Nagai | 701/109 |
| 4,825,837 | 5/1989 | Nakagawa | 123/681 |
| 4,837,698 | 6/1989 | Amano et al. | 364/431.053 |
| 4,905,652 | 3/1990 | Nakajima et al. | 123/679 |
| 4,908,765 | 3/1990 | Murakami et al. | 701/103 |
| 4,915,813 | 4/1990 | Nakajima et al. | 123/489 |
| 4,938,196 | 7/1990 | Hoshi et al. | 73/23.32 |
| 4,993,392 | 2/1991 | Tanaka et al. | 73/23.32 |
| 5,052,361 | 10/1991 | Ono et al. | 123/688 |
| 5,053,968 | 10/1991 | Uchinami | 701/104 |
| 5,265,458 | 11/1993 | Usami et al. | 73/23.32 |
| 5,323,635 | 6/1994 | Ueno et al. | 73/23.32 |
| 5,340,462 | 8/1994 | Suzuki | 123/688 |
| 5,394,857 | 3/1995 | Yamakawa | 123/686 |
| 5,417,099 | 5/1995 | Ohuchi | 73/23.32 |
| 5,461,902 | 10/1995 | Iwata | 73/23.32 |
| 5,473,889 | 12/1995 | Ehard et al. | 60/276 |
| 5,480,535 | 1/1996 | Kondo et al. | 204/425 |
| 5,483,795 | 1/1996 | Katoh et al. | 60/276 |
| 5,566,071 | 10/1996 | Akazaki et al. | 701/103 |
| 5,600,056 | 2/1997 | Hasegawa et al. | 73/117.2 |
| 5,610,321 | 3/1997 | Shinmoto | 73/23.32 |

FOREIGN PATENT DOCUMENTS 62-214249   9/1987   Japan .

*Primary Examiner*—Jacques H. Louis-Jacques
*Attorney, Agent, or Firm*—Kenyon & Kenyon

[57]                ABSTRACT

An air-fuel ratio detecting device and a method capable of correctly and very precisely detecting the air-fuel ratio of an internal combustion engine. The air-fuel ratio detecting device comprises an air-fuel ratio sensor disposed in the exhaust system of an internal combustion engine, an air-fuel ratio sensor circuit which applies a voltage to the air-fuel ratio sensor, detects the current through the air-fuel ratio sensor and produces an output that varies in proportion to the magnitude of the current that is detected, and a storage means for storing the data of a conversion map which is used for calculating the air-fuel ratio of the internal combustion engine in response to the output of the air-fuel ratio sensor circuit. The air-fuel ratio detecting device further comprises a circuit error detection means for detecting an error in the output caused by the air-fuel ratio sensor circuit, and a map calibration means for calibrating the data of the conversion map stored in the storage means based upon the error in the output detected by the circuit error detection means.

4 Claims, 6 Drawing Sheets

AIR-FUEL RATIO DETECTING DEVICE AND METHOD

BACKGROUND OF THE INVENTION

1. Field of the Invention

The present invention relates to an air-fuel ratio detecting device and a method and, particularly, to an air-fuel ratio detecting device which correctly and very precisely detects the air-fuel ratio of an internal combustion engine based upon the characteristics of each air-fuel ratio sensor and each air-fuel ratio sensor circuit.

2. Description of the Related Art

There has been known a linear air-fuel ratio sensor which is disposed in the exhaust system of an internal combustion engine (hereinafter referred to as an engine), detects the air-fuel ratio of the engine from the exhaust gas of the engine and generates an output which varies in proportion to the air-fuel ratio that is detected. In a device for controlling the air-fuel ratio by feedback by using the air-fuel ratio sensor, a map for calculating the air-fuel ratio of the engine in response to the output of the air-fuel ratio sensor is formed in advance through a bench test, the formed map is stored in a storage circuit, the air-fuel ratio of the engine is calculated from the map and from the output of the air-fuel ratio sensor mounted on the real engine, and the air-fuel ratio of the engine is so controlled by feedback as to approach the stoichiometric air-fuel ratio which most purifies the exhaust gas.

However, the processing circuit (hereinafter simply referred to as the air-fuel ratio sensor circuit) for processing the output of the air-fuel ratio sensor for forming the map used for the bench test, is different from the air-fuel ratio sensor circuit that is really used for the engine. Therefore, the air-fuel ratio that is really detected from the engine does not serve as a correct value. According to a method of correcting the output of an oxygen concentration (air-fuel ratio) sensor of an internal combustion engine disclosed in Japanese Unexamined Patent Publication (Kokai) No. 62-214249, the data of a map for calculating the air-fuel ratio of the engine in response to the output of the air-fuel ratio sensor, are corrected based on the output of the air-fuel ratio sensor. Though an error in the characteristics of the air-fuel ratio sensor has been taken into consideration, however, an error in the characteristics of the air-fuel ratio sensor circuit has not been taken into consideration. Therefore, though the output characteristics of each air-fuel ratio sensor are corrected, the idea is based on a prerequisite that no error is contained in the output at the stoichiometric air-fuel ratio; i.e., the output corresponding to the stoichiometric air-fuel ratio is not corrected.

According to the method of correcting the output of the air-fuel ratio sensor of an internal combustion engine disclosed in the above Japanese Unexamined Patent Publication (Kokai) No. 62-214249, the output of the air-fuel ratio sensor corresponding to the stoichiometric air-fuel ratio is set to be the same for all air-fuel ratio sensors without taking into consideration an error that exists in the air-fuel ratio sensor circuit. Therefore, the air-fuel ratio of the engine is not correctly and precisely detected, lacks reliability in controlling the air-fuel ratio by feedback and makes it difficult to purify the exhaust gas of the engine to a high degree.

SUMMARY OF THE INVENTION

It is therefore an object of the present invention to provide an air-fuel ratio detecting device and a method which is capable of correctly and precisely detecting the air-fuel ratio of an engine by correcting an error in the output caused by the air-fuel ratio sensor circuit, by solving the above-mentioned problems.

FIG. 1 is a diagram illustrating the constitution of fundamental blocks according to the present invention, wherein an air-fuel ratio detecting device 1 of the present invention is surrounded by a broken line. In order to accomplish the above-mentioned object of the present invention, the air-fuel ratio detecting device 1 comprises an air-fuel ratio sensor 20 composed of a solid electrolyte which is disposed in the exhaust system of an internal combustion engine 10 and passes an electric current when a voltage is applied thereto, an air-fuel ratio sensor circuit 30 which applies a voltage to the air-fuel ratio sensor 20, detects the current and generates an output that varies in proportion to the magnitude of the current, and a storage means 40 for storing the data of a conversion map which is used for calculating the air-fuel ratio of the internal combustion engine 10 in response to the output of the air-fuel ratio sensor circuit 30. The air-fuel ratio detecting device 1 of the present invention further comprises a circuit error detection means 50 for detecting an error in the output caused by the air-fuel ratio sensor circuit 30, and a map calibration means 60 for calibrating the data of the conversion map stored in the storage means 40 based upon the error in the output detected by the circuit error detection means 50.

Here, an air-fuel ratio control device comprises, in addition to the air-fuel ratio detecting device 1, a real air-fuel ratio calculation means 80 for calculating a real air-fuel ratio from the conversion map stored in the storage means 40 and from the output of the air-fuel ratio sensor circuit 30, and a fuel injection control means 90 for controlling the amount of fuel injected into the internal combustion engine 10 depending upon the real air-fuel ratio calculated by the real air-fuel ratio calculation means 80 in accordance with the operation condition of the internal combustion engine 10, so that the air-fuel ratio approaches, for example, the stoichiometric air-fuel ratio.

The circuit error detection means 50 in the air-fuel ratio detecting device according to the present invention comprises an inactivity determining means 51 for determining whether the air-fuel ratio sensor 20 is in an inactive state or not, and an error calculation means 52 for calculating the difference between an output of the air-fuel ratio sensor circuit 30 when it is determined that the air-fuel ratio sensor 20 is in the inactive state and an output of the air-fuel ratio sensor circuit 30 which output corresponds to the stoichiometric air-fuel ratio calculated from the conversion map.

The inactivity determining means 51 in the air-fuel ratio detecting device according to the present invention comprises a low-temperature start discrimination means 53 for discriminating whether the internal combustion engine 10 is started in a low-temperature condition or not, an output change rate calculation means 54 for calculating the rate of change in the output of the air-fuel ratio sensor circuit 30 when the internal combustion engine 10 is started in the low-temperature condition, and an output stability determining means 55 for determining that the output of the air-fuel ratio sensor circuit 30 is stabilized when the rate of change becomes smaller than a predetermined value.

When a voltage is applied by the air-fuel ratio sensor circuit 30 to the air-fuel ratio sensor 20 composed of a solid electrolyte disposed in the exhaust system, the air-fuel ratio sensor 20 passes an electric current that varies depending upon the air-fuel ratio. The air-fuel ratio sensor circuit 30 generates an output that varies in proportion to the current. An air-fuel ratio corresponding to the output of the air-fuel ratio sensor circuit 30, relying upon the map stored in the storage means 40, is read. Furthermore, an error in the output caused by the air-fuel ratio sensor circuit 30 is detected by the circuit error detection means 50, and the map calibration means 60 calibrates the data of the map based upon the error in the output. Therefore, the air-fuel ratio corresponding to the output value of the air-fuel ratio sensor circuit 30 is read from the calibrated map, to thereby correct the circuit error.

The circuit error detection means 50 in the air-fuel ratio detecting device of the present invention determines whether the air-fuel ratio sensor 20 is in an inactive state or not by utilizing the inactive state determining means. The air-fuel ratio sensor generates no current at the stoichiometric air-fuel ratio. The air-fuel ratio sensor 20 generates no current even when it is determined that the air-fuel ratio sensor 20 is in the inactive state. It can therefore be regarded that the output of the air-fuel ratio sensor circuit 30 at this moment corresponds to the stoichiometric air-fuel ratio. Moreover, the circuit error detection means 50 in the air-fuel ratio detecting device of the present invention calibrates the data of the conversion map by calculating, using the error calculation means 52, the difference between an output of the air-fuel ratio sensor circuit 30 that corresponds to the stoichiometric air-fuel ratio on the conversion map formed in advance by using the air-fuel ratio sensor circuit 30 for a bench test and an output of the air-fuel ratio sensor circuit 30 that is mounted on a real engine when the air-fuel ratio sensor 20 is detected to be in the inactive state. It is therefore possible to correctly detect the air-fuel ratio of the internal combustion engine 10.

In the inactivity determining means 51 of the air-fuel ratio detecting device of the present invention, the low-temperature start discrimination means 53 discriminates whether the internal combustion engine 10 is being started in a low-temperature condition or not, the output change rate calculation means 54 calculates a rate of change in the output of the air-fuel ratio sensor circuit 30 when the internal combustion engine 10 is started in the low-temperature condition, and the output stability determining means 55 determines that the output of the air-fuel ratio sensor circuit 30 is stabilized when the rate of change becomes smaller than a predetermined value. Therefore, the data of the conversion map are calibrated based upon the stabilized output of the air-fuel ratio sensor circuit 30, making it possible to detect the air-fuel ratio of the internal combustion engine 10 with high precision.

A method for detecting an air-fuel ratio of a combustion engine of the present invention uses an air-fuel ratio sensor, an air-fuel ratio sensor circuit and a storage means for storing the data of a conversion map. The air-fuel ratio sensor composed of a solid electrolyte which is disposed in the exhaust system of an internal combustion engine and generates an electric current when a voltage is applied thereto. The air-fuel ratio sensor circuit, which applies a voltage to the air-fuel sensor, detects the current and generates an output that varies in proportion to the magnitude of the current. The storage means for storing the data of a conversion map which is used for calculating the air-fuel ratio of the internal combustion engine in response to the output of the air-fuel ratio sensor circuit. The air-fuel ratio detecting method of the present invention comprising the steps of a circuit error detecting step in which an error in the output caused by the air-fuel ratio sensor circuit is detected, and a map calibration step in which the data of said conversion map are calibrated based upon the error in the output.

In the method for detecting an air-fuel ratio of a combustion engine of the present invention, the circuit error detecting step comprises the steps of an inactivity determining step in which whether the air-fuel ratio sensor is in an inactive state or not is determined; and an error calculating step in which a difference between an output of the air-fuel ratio sensor circuit of when it is determined that said air-fuel ratio sensor is in the inactive state and an output of said air-fuel ratio sensor circuit that corresponds to the stoichiometric air-fuel ratio calculated from said conversion map, is calculated.

In the method for detecting an air-fuel ratio of a combustion engine of the present invention, the inactivity determining step comprises the steps of:

a low-temperature start discrimination step in which whether the internal combustion engine is started in a low-temperature condition or not is discriminated;

an output change rate calculating step in which the rate of change in the output of the air-fuel ratio sensor circuit when the internal combustion engine is started in the low-temperature condition, is calculated; and an output stability determining step in which it is determined that the output of said air-fuel ratio sensor circuit is stabilized when the rate of change becomes smaller than a predetermined value.

BRIEF DESCRIPTION OF THE DRAWINGS

The present invention will be more clearly understood from the description as set forth below with reference to the accompanying drawings, wherein.

DESCRIPTION OF THE PREFERRED EMBODIMENTS

Figure 1:
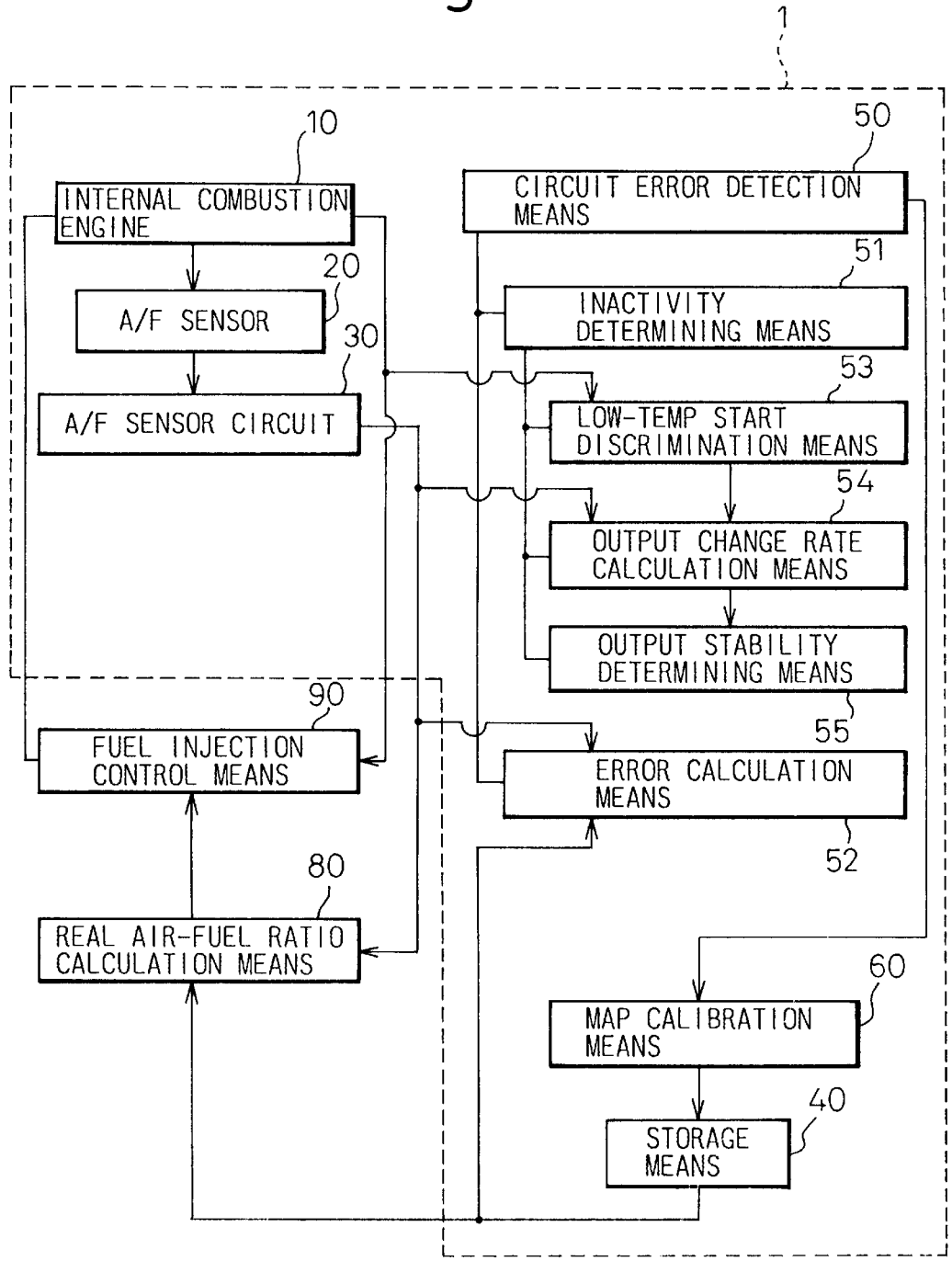
FIG. 1 is a diagram illustrating the constitution of fundamental blocks according to the present invention.
Figure 2:
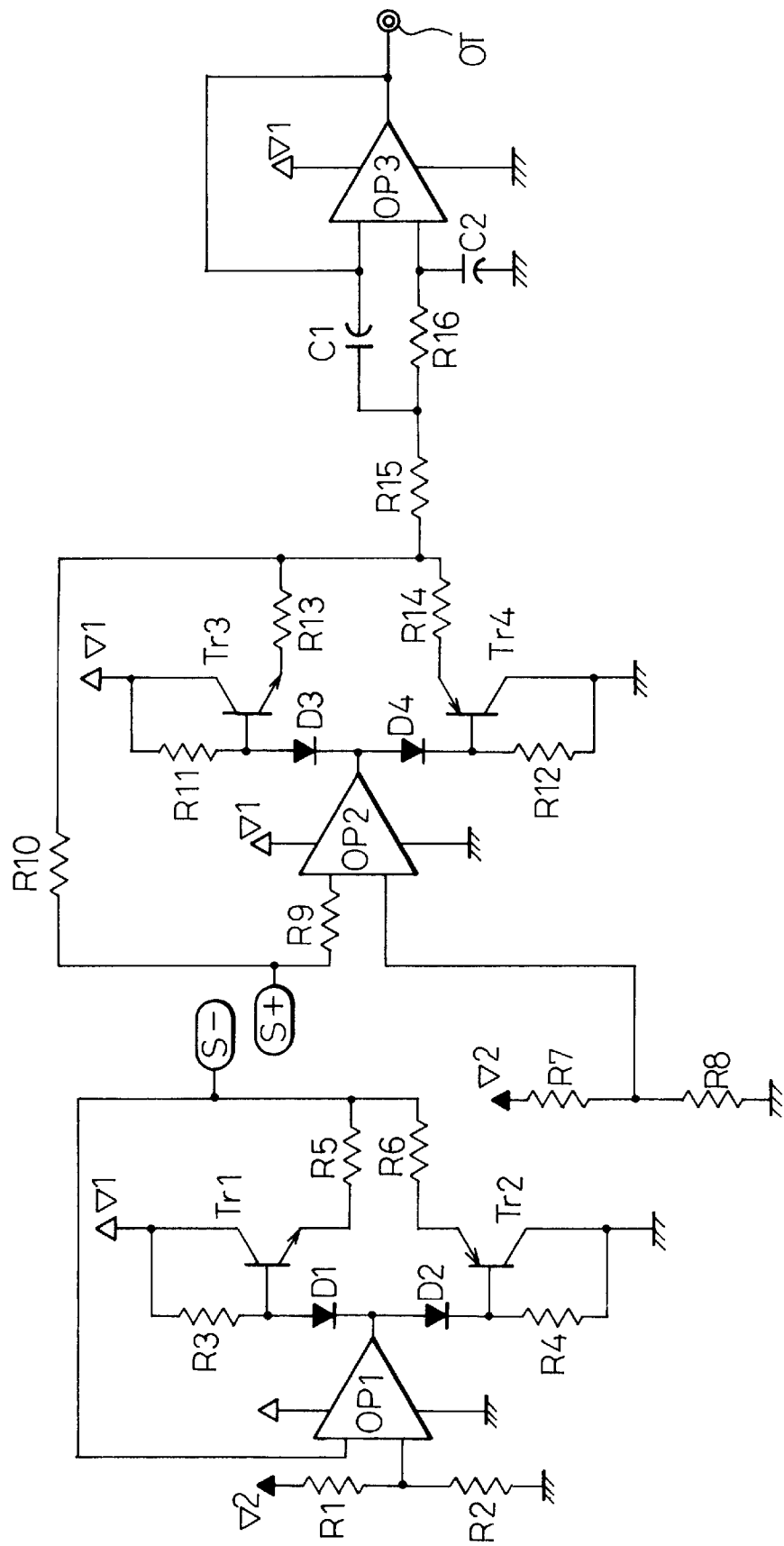
FIG. 2 is a diagram illustrating an air-fuel ratio sensor circuit employed by an embodiment.

FIG. 2 is a diagram, illustrating an air-fuel ratio sensor circuit employed in an embodiment, wherein reference numerals R1 to R16 denote resistors, C1 and C2 denote capacitors, D1 to D4 denote diodes, Tr1 to Tr4 denote transistors, and OP1 to OP3 denote operational amplifiers. Constant voltages V1 and V2 are applied to the air-fuel ratio sensor circuit, and an air-fuel ratio sensor that is not shown is connected between electrodes S+ and S– that are shown between the operational amplifiers OP1 and OP2. Then, a constant voltage set by the operational amplifier OP1 is applied to the air-fuel ratio sensor connected across the above electrodes. The resistor R10 works to detect an electric current generated by the air-fuel ratio sensor. The voltage V1 is applied to drive the transistors Tr1 to Tr4, operational amplifiers OP1 to OP3, and the air-fuel ratio sensor. A voltage V2 is applied as a very precise reference voltage to the operational amplifiers OP1 and OP2. The voltage V2 is about 5 volts, and a voltage, of 3.0 volts divided by the resistors R1, R2, is input to the operational amplifier OP1, and a voltage of 3.3 volts divided by the resistors R7, R8 is input to the operational amplifier OP2. The air-fuel ratio sensor connected across the electrodes S+ and S− is disposed in the exhaust system of an engine. The air-fuel ratio sensor composed the internal current of a solid electrolyte changes upon being exposed to the exhaust gas of the engine. The operational amplifier OP2 changes its output depending upon a change in the current generated by the air-fuel ratio sensor. The air-fuel ratio sensor generates no internal current when the exhaust gas of the engine has the stoichiometric air-fuel ratio or when the air-fuel ratio sensor is in an inactive state. Therefore, the output of the operational amplifier OP2 at this moment is equal to the input voltage of 3.3 volts. Next, the output of the operational amplifier OP2 is input to the operational amplifier OP3 in the integration circuit, whereby a voltage without a transient change is output from the output terminal OT of the air-fuel ratio sensor circuit depending upon the air-fuel ratio in the engine.

Figure 3:
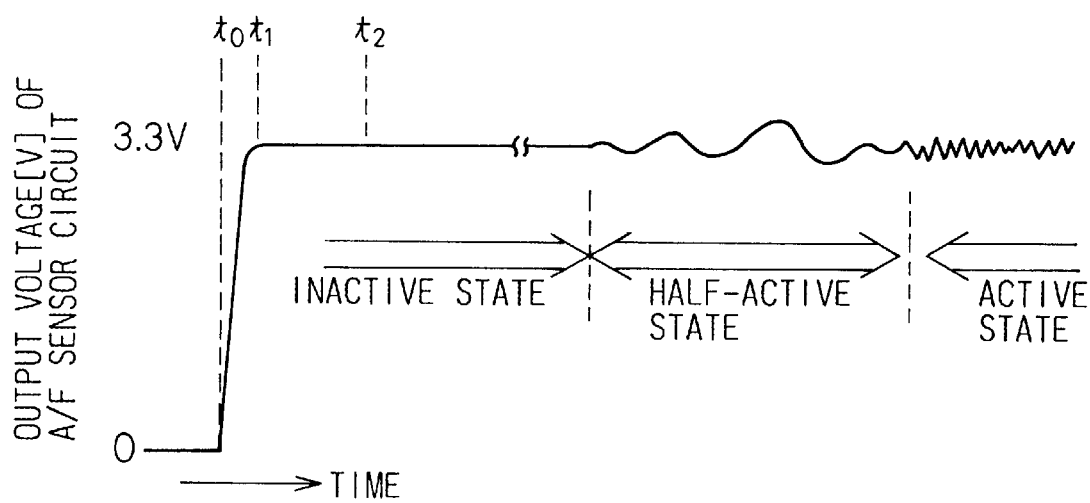
FIG. 3 is a diagram illustrating output waveforms of the air-fuel ratio sensor circuit immediately after the start of an engine.

FIG. 3 is a diagram illustrating output waveforms of the air-fuel ratio sensor circuit immediately after the start of the engine, wherein the abscissa represents the time and the ordinate represents the output voltage of the air-fuel ratio sensor circuit. When the engine is started at a moment $t_0$, a voltage is applied from a battery to the air-fuel ratio sensor circuit and to the air-fuel ratio sensor, and the output voltage of the air-fuel ratio sensor circuit suddenly rises from 0 volt at the moment $t_0$ to 3.3 volts at a moment $t_1$, for example, 3 seconds later. The output voltage of the air-fuel ratio sensor circuit remains constant at 3.3 volts as long as the air-fuel ratio sensor is in the inactive state. As the air-fuel ratio sensor becomes partially active, however, the output voltage fluctuates at a low frequency, with 3.3 volts as a center, as shown. Then, as the air-fuel ratio sensor becomes active, the output voltage fluctuates at a high frequency with 3.3 volts as a center. As described earlier, the output current generated by the air-fuel ratio sensor becomes zero when the exhaust gas detected by the air-fuel ratio sensor has the stoichiometric air-fuel ratio or when the air-fuel ratio sensor is in the inactive state. By reading the output voltage of 3.3 volts of the air-fuel ratio sensor circuit at this moment, therefore, it is possible to detect the output voltage, i.e., the stoichiometric voltage of the air-fuel ratio sensor circuit when the air-fuel ratio sensor has detected the exhaust gas of the engine having the stoichiometric air-fuel ratio. According to the present invention, as will be described later, the stoichiometric voltage is found as an average output voltage of the air-fuel ratio sensor circuit from, for example, the moment $t_1$ to a moment $t_2$ of 5 seconds later.

Figure 4:
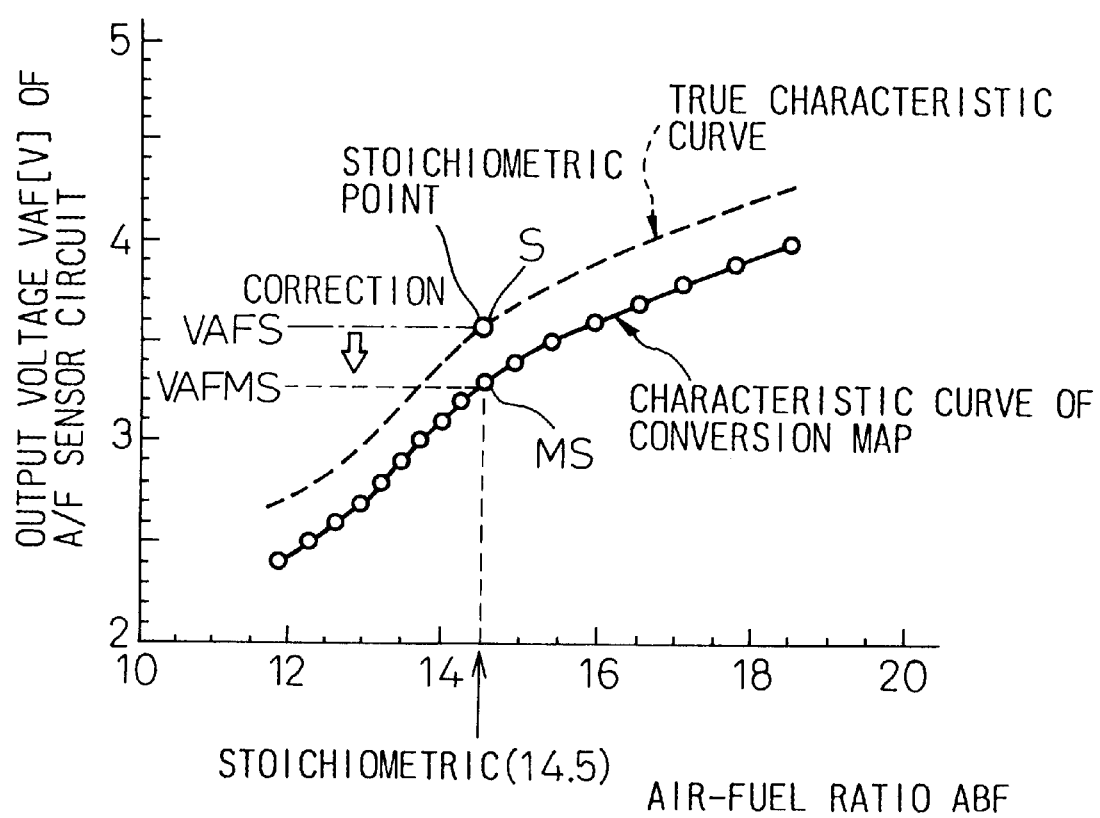
FIG. 4 is a diagram illustrating a conversion map of air-fuel ratios of an internal combustion engine corresponding to the outputs of the air-fuel ratio sensor circuit.

FIG. 4 is a diagram illustrating a conversion map of the air-fuel ratios of an engine corresponding to the outputs of the air-fuel ratio sensor circuit. In FIG. 4, the abscissa represents the air-fuel ratio ABF of the engine detected by the air-fuel ratio sensor and the ordinate represents the output voltage VAF of the air-fuel ratio sensor circuit. In FIG. 4, a thick solid line represents a characteristic curve of the conversion map formed in advance, by bench testing, in order to calculate the air-fuel ratios of the engine in response to the outputs of the air-fuel ratio sensor circuit. The data for forming the conversion map are measured in advance, by bench testing, by using a standard air-fuel ratio sensor and a standard air-fuel ratio sensor circuit, and are stored in the storage circuit RAM. In FIG. 4, a broken line represents a characteristic curve of a true air-fuel ratio sensor circuit formed in a manner as described below. First, a point S is plotted at which the output voltage VAF of the air-fuel ratio sensor circuit is a stoichiometric voltage VAFS that is measured by using the air-fuel ratio sensor and the air-fuel ratio sensor circuit that are mounted on the real engine and the air-fuel ratio is the stoichiometric, i.e., 14.5. Next, a point MS is plotted that corresponds to the stoichiometric air-fuel ratio 14.5 on the characteristic curve of the conversion map represented by the thick line, and the output voltage of the air-fuel ratio sensor circuit corresponding to this point is denoted by VAFMS. Then, a plurality of points are plotted that are shifted in the direction of ordinate by VAFS− VAFMS along the characteristic curve of the conversion map, and the thus plotted points are connected by broken lines to form a true characteristic curve of the air-fuel ratio sensor circuit. The output voltages VAF of the air-fuel ratio sensor circuit that are measured on the real engine accord to the characteristic curve represented by this broken line. That is, the output voltage VAF of the air-fuel ratio sensor circuit is read, VAF−(VAFS−VAFMS) is calculated to update VAF, and the air-fuel ratio is read on the characteristic curve of the conversion map that is formed in advance, by bench testing, in accordance with the updated VAF, thereby to calculate the air-fuel ratio of the real engine at that moment.

Figure 5:
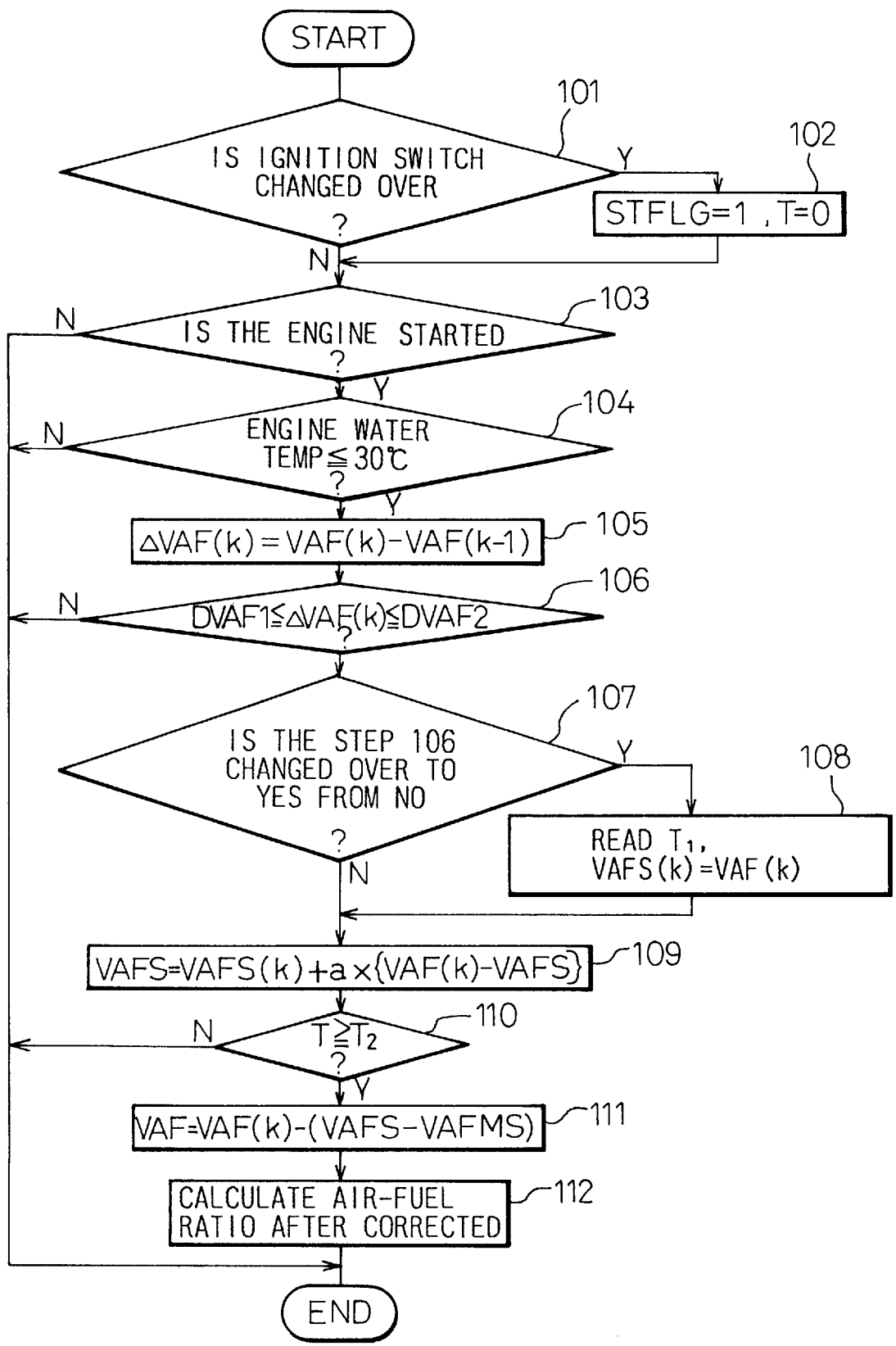
FIG. 5 is a flow chart of a map calibration routine according to a first embodiment.

FIG. 5 is a flow chart of a map calibration routine according to a first embodiment. This flow chart illustrates the routine for calibrating the conversion map depending upon the air-fuel ratio sensor and the air-fuel ratio sensor circuit that are used for the real engine. This routine is executed for every predetermined crank angle of the engine, for example, for every 180° CR or for every predetermined period of time. First, a step 101 discriminates whether the ignition switch is changed over from off to on or not. When the result of the discrimination is yes, the routine proceeds to a step 102 and when the result of the discrimination is no, the routine proceeds to a step 103. At the step 102, the start flag STFLG, that has been initially set to 0, is set to 1, a timer T is set to 0, and the routine proceeds to the step 103 where it is discriminated whether the engine is started or not relying upon whether the number of revolutions NE of the engine calculated from a signal output from a crank angle sensor that detects the crank angle of the engine has exceeded 400 rpm or not. When NE $\geq$400 rpm, it is discriminated that the engine has started and the routine proceeds to a step 104. When NE <400 rpm, the routine ends. At the step 104, the active state of the air-fuel ratio sensor is determined based on the water temperature TW that is read by a water temperature sensor which is embedded in the engine block and detects the temperature of the engine. That is, when the water temperature TW is $\leq$30° C., it is so determined that the engine is in the cold start condition and the air-fuel ratio sensor is in the inactive state, and the routine proceeds to a step 105. When the water temperature TW is >30° C., it is so determined that the engine is in the warm condition and the air-fuel ratio sensor is in the active state, and the routine ends.

At the step 105, the output voltage VAF of the air-fuel ratio sensor circuit is read to calculate a difference $\Delta VAF_{(K)}$ =$VAF_{(K)}$ −$VAF_{(K-1)}$ between the previous value $VAF_{(K-1)}$ and the value $VAF_{(K)}$ of this time, and the routine proceeds to a step 106 where it is discriminated whether $\Delta VAF_{(K)}$ calculated at the step 105 lies within a predetermined range (DVAF1 $\leq \Delta VAF_{(K)} \leq$ DVAF2) or not. When the result of discrimination is yes, the routine proceeds to a step 107.

When the result is no, the routine ends. As shown in FIG. 3, the output voltage VAF of the air-fuel ratio sensor circuit rises at a moment $t_0$ when the operation of the engine is started and reaches the stoichiometric voltage and saturates at a moment $t_1$, so that $\Delta VAF_{(K)}$ becomes nearly 0. Therefore, the step 106 detects the output voltage VAF of the air-fuel ratio sensor circuit that has saturated after the engine is operated. Here, DVAF1 and DVAF2 are set to be, for example, 0.01 volt and 0.02 volts.

At the step 107, it is discriminated whether the result of discrimination at the step 106 is changed over to yes from no or not. When the result of discrimination is yes, the routine proceeds to a step 108. When the result is no, the routine proceeds to a step 109. At the step 108, the timer $T=T_1$ (about 3 seconds) is read, the output voltage $VAF_{(K)}$ of the air-fuel ratio sensor circuit at this time is substituted for $VAFS_{(K)}$, and the routine proceeds to the step 109 where the stoichiometric voltage VAFS is calculated in accordance with the following equation, $$VAFS = VAFS_{(K)} + a(VAF_{(K)} - VAFS)$$

where a is a moving average constant of, for example, 0.1.

The first stoichiometric voltage VAFS that is saturated first when the timer is $T=T_1$ (moment $t_1$ shown in FIG. 3) after the engine is operated, becomes equal to the voltage $VAF_{(K)}$ from which the output voltage VAF of the air-fuel ratio sensor circuit is read. Thereafter, the stoichiometric voltages VAFS calculated in the subsequent routines are found as average values of the voltages $VAF_{(K)}$ that are read in the routines as represented by the above-mentioned equation.

At a step 110, it is discriminated whether the timer is $T=T_2$ (about 8 seconds) after the engine is started. When the result of discrimination is yes, the routine proceeds to a step 111. When the result is no, the routine ends. At a step 111, the output voltage VAF of the air-fuel ratio sensor circuit is calibrated in accordance with the following equation based upon the stoichiometric voltage VAFS found at the step 109, upon the output voltage VAFMS of the reference air-fuel ratio sensor circuit corresponding to, for example, the stoichiometric air-fuel ratio 14.5 on the conversion map that has been found in advance by the bench test using the reference air-fuel ratio sensor and the reference air-fuel ratio sensor circuit, and upon the output voltage $VAF_{(K)}$ of the air-fuel ratio sensor circuit detected this time, $$VAF = VAF_{(K)} - (VAFS - VAFMS)$$

and the routine proceeds to a step 112.

At the step 112, the air-fuel ratio of the engine corresponding to the output voltage VAF of the air-fuel ratio sensor circuit found by the calibration at the step 111, is calculated, i.e., the air-fuel ratio after being corrected is calculated based on the conversion map that has been formed in advance and has been stored in a storage circuit such as RAM. This corresponds to finding a characteristic curve represented by a broken line in FIG. 4 by shifting a characteristic curve of the conversion map formed in advance by the bench test represented by a solid line in FIG. 4 toward the output voltage $VAF_{(K)}$ of the air-fuel ratio sensor circuit detected at this time by VAFS−VAFMS.

Figure 6:
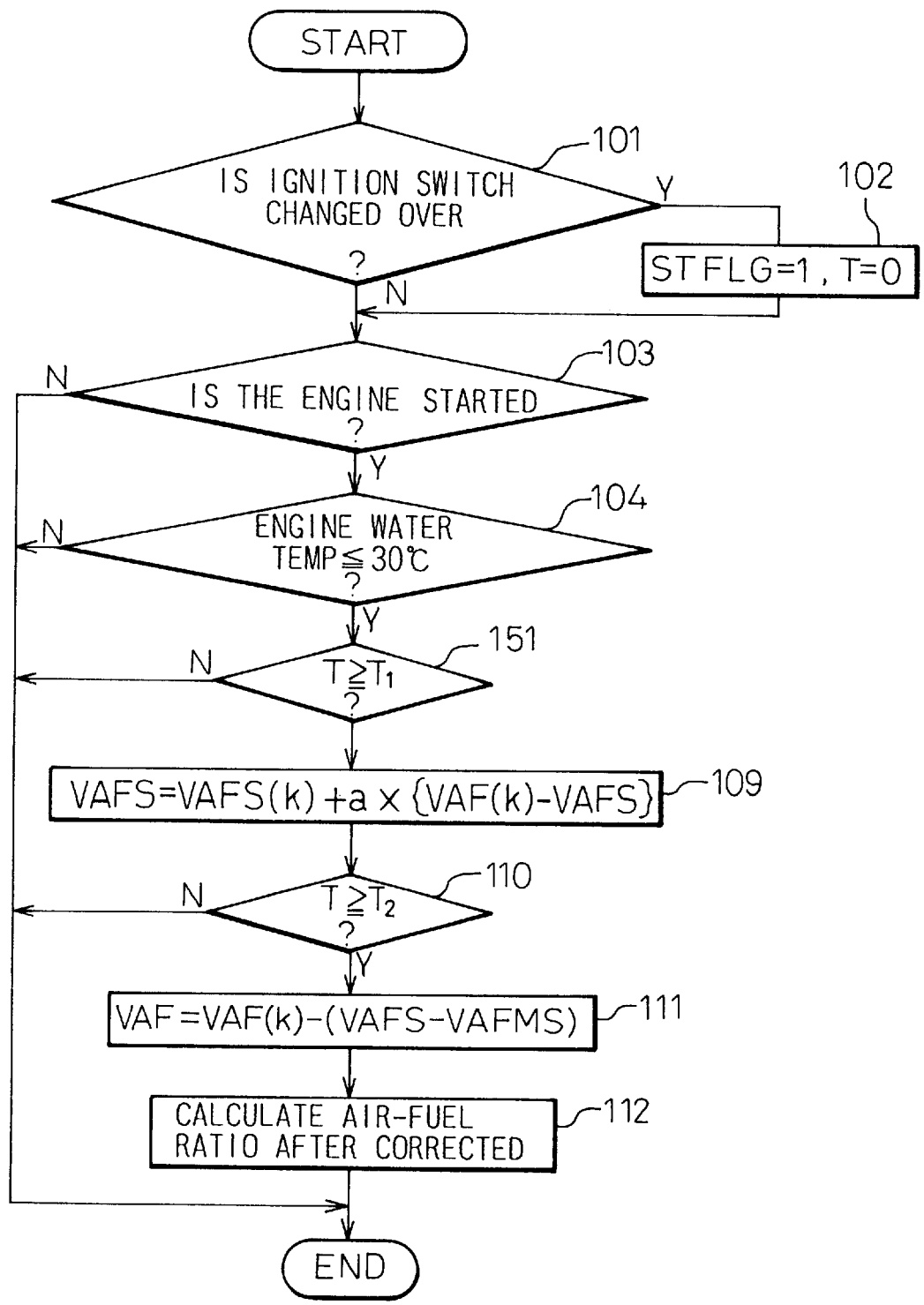
FIG. 6 is a flow chart of a map calibration routine according to a second embodiment.

FIG. 6 is a flow chart of a map calibration routine according to a second embodiment. The steps 105 to 108 in the flow chart of FIG. 5 are substituted for a step 151. Therefore, the step 151 only will be described. The step 151 discriminates whether the timer T is greater than $T_1$. When the result of discrimination is yes, the routine proceeds to the step 109. When the result is no, the routine ends. By so setting the timer that $T_1$ is 3 seconds and $T_2$ is 8 seconds from the results of experiment, it is possible to find the output voltage of the air-fuel ratio sensor circuit in the inactive state, i.e., to find the stoichiometric voltage as explained with reference to FIG. 3. In the second embodiment, the average output voltage of the air-fuel ratio sensor circuit of from the moment $T_1$ to the moment $T_2$ is found as a stoichiometric voltage.

According to the air-fuel ratio detecting device and a method of the present invention as described above, it is possible to correctly and very precisely detect the air-fuel ratio of an internal combustion engine. By controlling the amount of fuel injection into the engine based upon the air-fuel ratio detected by the device of the present invention, furthermore, it is possible to further purify the exhaust gas of the engine. According to the air-fuel ratio detecting device of the present invention which calibrates the conversion map while the engine is in operation depending upon the output characteristics of the air-fuel ratio sensor circuit mounted on a real engine, furthermore, no step is required for calibrating the map at the time of shipment of the real engine.

According to the air-fuel ratio detecting device and a method of the present invention, furthermore, the output of the air-fuel ratio sensor circuit at the stoichiometric air-fuel ratio is read from the nonactive state of the air-fuel ratio sensor in order to calibrate the conversion map. Therefore, there is no need to separately provide the oxygen sensor of the type of concentration cell which is capable of very precisely detecting the stoichiometric air-fuel ratio as an air-fuel ratio sensor for calibration, and it is possible to provide an air-fuel ratio detecting device at a reduced cost.

According to the air-fuel ratio detecting device and a method of the present invention in which the data of the conversion map are calibrated based on the stabilized outputs of the air-fuel ratio sensor circuit, it is possible to very precisely detect the air-fuel ratio of the engine.

It should be further understood by those skilled in the art that the foregoing description is concerned with preferred embodiments of the disclosed device and that various changes and modifications may be made in the invention without departing from the spirit and scope thereof.

I claim:

1. An air-fuel ratio detecting device comprising:

an air-fuel ratio sensor composed of a solid electrolyte which is disposed in an exhaust system of an internal combustion engine and passes an electric current when a voltage is applied thereto;

an air-fuel ratio sensor circuit which applies a voltage to the air-fuel ratio sensor, detects the current and generates an output that varies in proportion to the magnitude of the current; and storage means for storing data in a conversion map which is used to calculate an air-fuel ratio of the internal combustion engine in response to the output of the air-fuel ratio sensor circuit;

inactivity determining means for determining whether the air fuel ratio sensor is in an inactive state;

circuit error detection means for detecting an error in the output as a difference between a reference output value and an output of the air-fuel ratio sensor circuit when the air-fuel ratio sensor is determined to be in the inactive state; and map calibration means for calibrating said conversion map so that an air-fuel ratio indicated by said conversion map is calculated based on the output value of the air-fuel ratio circuit and the error detected by said circuit error detection means.

2. An air-fuel ratio detecting device according to claim 1, wherein said inactivity determining means comprises:

a low temperature start discrimination means for determining whether the internal combustion engine is started in a low-temperature condition;

an output change rate calculation means for calculating the rate of change in the output of the air-fuel ratio sensor circuit when the internal combustion engine is started in the low-temperature condition;

an output stability determining means for determining that the output of said air-fuel ratio sensor circuit is stabilized when the rate of change becomes smaller than a predetermined value;

wherein said inactivity determining means determining that the air-fuel ratio sensor is in an inactive state when said output stability determining means determined that the output of said air-fuel ratio sensor circuit is stabilized.

3. A method for detecting an air-fuel ratio of a combustion engine using: an air-fuel ratio sensor composed of a solid electrolyte which is disposed in the exhaust system of an internal combustion engine and passes an electric current when a voltage is applied thereto; an air-fuel ratio sensor circuit which applies a voltage to the air-fuel sensor, detects the current and generates an output that varies in proportion to the magnitude of the current; and a storage means for storing the data of a conversion map which is used for calculating the air-fuel ratio of the internal combustion engine in response to the output of the air-fuel ratio sensor circuit, said air-fuel ratio detecting method comprising the steps of:

determining whether the air-fuel ratio sensor is in an inactive state;

a circuit error detecting step in which an error in the output caused by the air-fuel ratio sensor circuit is detected as a difference between a reference output value and an output value of the air-fuel ratio sensor circuit when the air-fuel ratio sensor is in the inactive state, and a map calibration step in which the data of said conversion map is calibrated so that an air-fuel ratio indicated by said conversion map is calculated based on the output value of the air-fuel ratio circuit and the error detected by said circuit error detection means.

4. A method for detecting an air-fuel ratio of a combustion engine according to claim 3, wherein said inactivity determining step comprises:

a low temperature start discrimination step in which a determination is made as to whether the internal combustion engine is started in a low-temperature condition;

an output change rate calculation step in which a determination is made of the rate of change in the output of the air-fuel ratio sensor circuit when the internal combustion engine is started in the low-temperature condition;

an output stability determining step in which it is determined that the output of said air-fuel ratio sensor circuit is stabilized when the rate of change becomes smaller than a predetermined value;

wherein it is determined in said inactivity determining step that the air-fuel ratio sensor is in an inactive state when it is determined in said output stability determining step that the output of said air-fuel ratio sensor circuit is stabilized.

* * * * *